(12) United States Patent
Takimoto et al.

(10) Patent No.: US 10,538,580 B2
(45) Date of Patent: Jan. 21, 2020

(54) ANTI-EQUOL ANTIBODY COMPOSITION AND USE THEREFOR

(71) Applicant: HEALTHCARE SYSTEMS CO., LTD., Nagoya-shi, Aichi (JP)

(72) Inventors: Yosuke Takimoto, Nagoya (JP); Keitaro Hagiwara, Nagoya (JP)

(73) Assignee: HEALTHCARE SYSTEMS CO., LTD., Nagoya-shi (JP)

( * ) Notice: Subject to any disclaimer, the term of this patent is extended or adjusted under 35 U.S.C. 154(b) by 0 days.

(21) Appl. No.: 16/465,731

(22) PCT Filed: Dec. 18, 2017

(86) PCT No.: PCT/JP2017/045376
§ 371 (c)(1),
(2) Date: May 31, 2019

(87) PCT Pub. No.: WO2018/117044
PCT Pub. Date: Jun. 28, 2018

(65) Prior Publication Data
US 2019/0300597 A1    Oct. 3, 2019

(30) Foreign Application Priority Data
Dec. 19, 2016    (JP) .................................. 2016-245952

(51) Int. Cl.
*G01N 33/53* (2006.01)
*C07K 16/16* (2006.01)

(52) U.S. Cl.
CPC .......... *C07K 16/16* (2013.01); *G01N 33/5308* (2013.01); *C07K 2317/33* (2013.01); *C07K 2317/565* (2013.01); *C07K 2317/92* (2013.01)

(58) Field of Classification Search
CPC ........................... G01N 33/5308; C07K 16/16
See application file for complete search history.

(56) References Cited

U.S. PATENT DOCUMENTS

2012/0064550 A1    3/2012    Minekawa et al.

FOREIGN PATENT DOCUMENTS

| JP | 2010-169507 A | 8/2010 |
| JP | 2011-106886 A | 6/2011 |
| JP | 2012-098034 A | 5/2012 |
| JP | 2014-160088 A | 9/2014 |

OTHER PUBLICATIONS

May 23, 2017 Office Action issued in Japanese Patent Application No. 2016-245952.
Minekawa, Takayuki et al., "The Development of S-Equol Diastereoisomer Specific ELISA", American Journal of Analytical Chemistry, 2012, vol. 3, pp. 448-454.
Houerou, Cyril Le et al., "Syntheses of Novel Hapten-Protein Conjygates for Production of Highly Specific Antibodies to Formononetin, Daidzein and Genistein", Tetrahedron, 2000, vol. 56, pp. 295-301.
Talbot, Duncan C. S. et al., "Monoclonal Antibody-Based Time-Resolved Fluorescence Immunoassays for Daidzein, Genistein, and Equol in Blood and Urine: Application to the Isoheart Intervention Study", Clinical Chemistry, 2007, vol. 53, pp. 748-756.
Feb. 6, 2018 Search Report issued in International Patent Application No. PCT/JP2017/045376.
Feb. 6, 2018 Written Opinion of the International Searching Authority issued in International Patent Application No. PCT/JP2017/045376.
Nov. 14, 2019 Extended Search Report issued in European Patent Application No. 17884415.5.
Niwa, T. et al., "Preparation of Soy Isoflavonoids for the Production of Anti-Equol Monoclonal Antibody", Phytochemistry Letters, vol. 2, No. 4, (2009), pp. 220-222.

*Primary Examiner* — Galina M. Yakovleva
(74) *Attorney, Agent, or Firm* — Oliff PLC

(57) ABSTRACT

An anti-equol antibody composition, containing an anti-equol antibody or antibody fragment thereof containing, as an immunoglobulin heavy chain variable region, hypervariable regions CDR1, CDR2, and CDR3 respectively including amino acid sequences represented by SEQ ID NO: 1-3, and as an immunoglobulin light chain variable region, hypervariable regions CDR1', CDR2', and CDR3' respectively including amino acid sequences represented by SEQ ID NO: 4-6; and an anti-equol antibody or antibody fragment thereof containing, as an immunoglobulin heavy chain variable region, hypervariable regions CDR1, CDR2, and CDR3 respectively including amino acid sequences represented by SEQ ID NO: 1-3, and as an immunoglobulin light chain variable region, hypervariable regions CDR1', CDR2', and CDR3' respectively including amino acid sequences represented by SEQ ID NO: 7-9.

15 Claims, 2 Drawing Sheets

Specification includes a Sequence Listing.

ANTI-EQUOL ANTIBODY COMPOSITION AND USE THEREFOR

TECHNICAL FIELD

The present specification relates to an anti-equol antibody composition and a use therefor.

BACKGROUND ART

Equol is a metabolite that is metabolized from an isoflavone by human and other animal's intestinal bacteria. Due to its antiestrogenic effects, equol is known to improve various symptoms caused by decreased female hormones.

Equol is produced by intestinal bacterial from soy bean products and the like, but the amount of equol produced may differ depending not only on the amount of soy beans ingested, but also on individual differences in intestinal flora. Equol may also be ingested directly. As equol exhibits antiestrogenic effects, and it is important to monitor both individual equol production ability (produced amounts) and the total amount of equol in the body.

A method has already been provided for using an anti-equol antibody to measure equol in urine (Patent Literature 1).

SUMMARY

However, the cross-reactivity, detection sensitivity and the like of anti-equol antibodies have not always been satisfactory. There is demand for ways of measuring equol easily and with high sensitivity and accuracy.

It is an object of the present specification to provide a more practical anti-equol antibody composition, and a use therefor.

As a result of exhaustive research, the inventors obtained a composition containing an anti-equol antibody having more satisfactory cross-reactivity and affinity and the like for equol. The present specification provides the following means based on these findings.

[1] An anti-equol antibody composition, comprising
an anti-equol antibody or antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 4, a hypervariable region CDR2' comprising the amino acid sequence represented by SEQ ID NO: 5 and a hypervariable region CDR3' comprising the amino acid sequence represented by SEQ ID NO: 6; and
an anti-equol antibody or antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 7, a hypervariable region CDR2' comprising the amino acid sequence represented by SEQ ID NO: 8 and a hypervariable region CDR3' comprising the amino acid sequence represented by SEQ ID NO: 9.

[2] A composition having 80% or more cross-reactivity, in total, to R-equol as compared to a cross-reactivity to S-equol as 100%.

[3] The composition according to [1] or [2], wherein cross-reactivity to R-equol is 85% or more.

[4] The composition according to any of [1] to [3], also having 0.01% or less cross-reactivity to one or two or more isoflavones selected from the group consisting of daidzein, genistein and glycitein.

[5] The composition according to [4], wherein cross-reactivity to each of the isoflavones including daidzein, genistein and glycitein is 0.01% or less.

[6] The composition according to any of [1] to [5], also having 1% or less cross-reactivity to one or two or more selected from the group consisting of ellagic acid dihydrate, catechin monohydrate and gallic acid.

[7] The composition according to [6], wherein cross-reactivity to ellagic acid dihydrate and catechin monohydrate is 0.01% or less.

[8] An equol detection reagent containing the composition according to any of [1] to [7].

[9] An anti-equol antibody or antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 4, a hypervariable region CDR2' comprising the amino acid sequence represented by SEQ ID NO: 5 and a hypervariable region CDR3' comprising the amino acid sequence represented by SEQ ID NO: 6.

[10] An anti-equol antibody or antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 7, a hypervariable region CDR2' comprising the amino acid sequence represented by SEQ ID NO: 8 and a hypervariable region CDR3' comprising the amino acid sequence represented by SEQ ID NO: 9.

[11] A method for measuring equol in a biological sample, comprising bringing the equol detection reagent according to [8] into contact with the equol in the biological sample.

[12] An equol measurement device including the detection reagent according to [8], wherein the detection reagent is bound to a solid-phase carrier.

[13] An equol measurement kit including the detection reagent according to [8].

[14] An expression vector containing a polynucleotide encoding for the antibody or antibody fragment thereof according to [9].

[15] An expression vector containing a polynucleotide encoding for the antibody or antibody fragment thereof according to [10].

DESCRIPTION OF EMBODIMENTS

Figure 1:
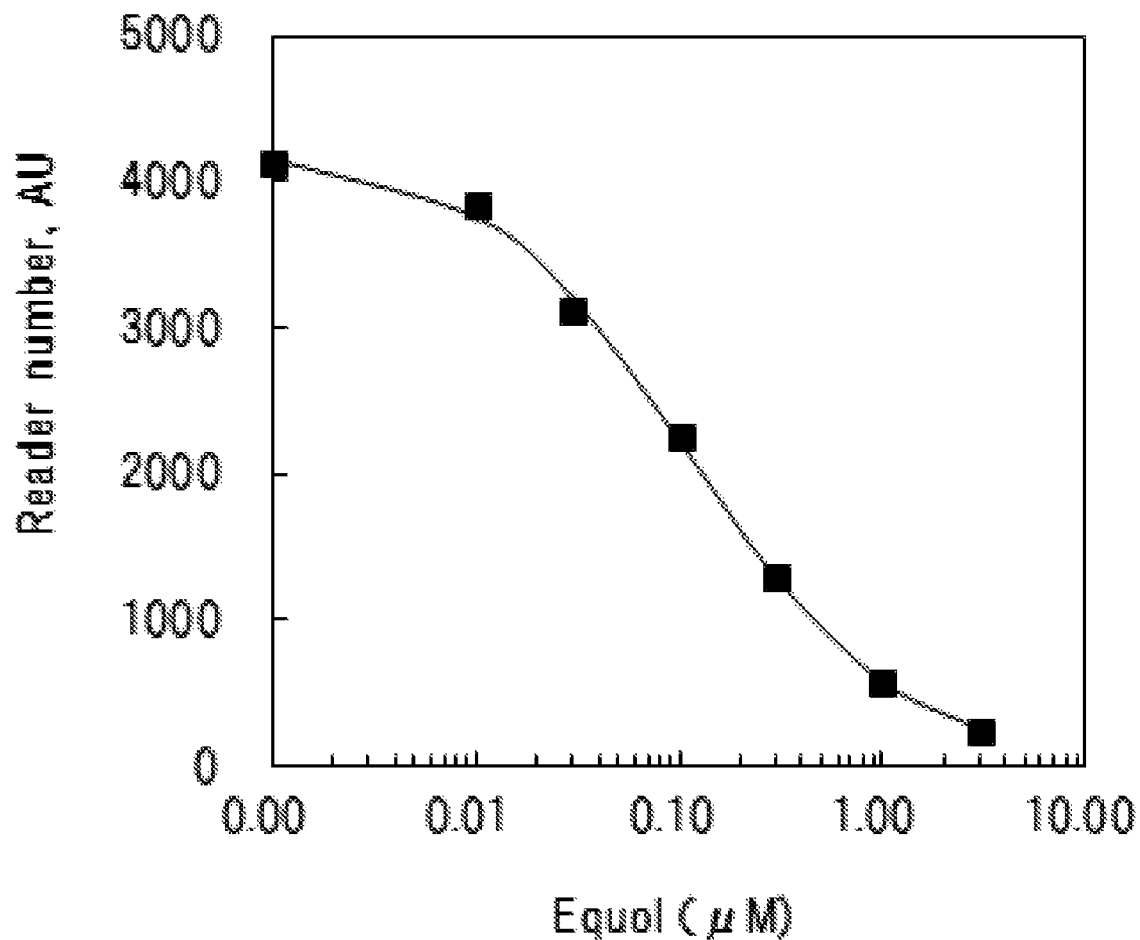
FIG. 1 shows evaluation results for antibody titer of an anti-equol monoclonal antibody.

The disclosures of this specification relate to an anti-equol antibody composition and a use therefor. With a composition (hereunder simply called the present antibody composition) containing the anti-equol monoclonal antibody (hereunder simply called the antibody) disclosed in this specification, equol can be measured accurately and with high detection sensitivity. Due to the high cross-reactivity, moreover, equol can be measured precisely and accurately in a biological sample.

The present antibody composition binds specifically to R-equol, but also has high binding ability to S-equol overall, and has high detection sensitivity for S-equol. It can thus measure equol easily even in biological samples with low equol content or in small-volume biological samples.

Typical and non-limiting specific examples of the present invention are explained in detail below with reference to appropriate drawings. These detailed explanations are simply intended to provide those skilled in the art with the details for implementing the preferred examples of the present invention, and are not intended to limit the scope of the invention. Moreover, the additional features and inventions disclosed below can be used separately or together with other features and inventions to provide a further improved anti-equol antibody composition and use therefor.

Furthermore, the combination of features and processes disclosed in the following detailed description is not indispensable for implementing the present invention in the broadest sense, and is only provided in order to explain representative examples of the present invention in particular. In addition, the various features of the typical examples above and below and the various features of the matter disclosed in the independent and dependent claims need not be combined in the same way or in the same order as in the specific examples described here when providing additional useful embodiments of the present invention.

All features described in this specification and/or the claims are intended to be disclosed individually and separately from one another as limitations on the specific matter disclosed and claimed at the time of the initial application, separately from the configuration of features described in the examples and/or claims. Moreover, all descriptions of numerical ranges and groups or populations are intended to include intermediate configurations thereof as limitations on the specific matter disclosed and claimed at the time of the initial application.

Embodiments of the anti-equol antibody composition and use therefor disclosed in this specification are explained in detail below.

(Anti-equol Antibody Composition)

The present antibody composition may contain two anti-equol monoclonal antibodies.

The specific binding abilities of the antibody composition obtained by combining these antibodies can be enumerated for example as follows. The antibody composition may have at least the specific binding ability of (1). It may also have any one or any two or more of the specific binding abilities of (2) to (4) below. In this specification, "specific binding ability" or "binding specifically" means binding ability and binding based on the antigen recognition ability of the antibody or in other words the immunoglobulin. The structures of R-equol and S-equol are shown below. Incidentally, intestinal bacteria exclusively produce S-equol.

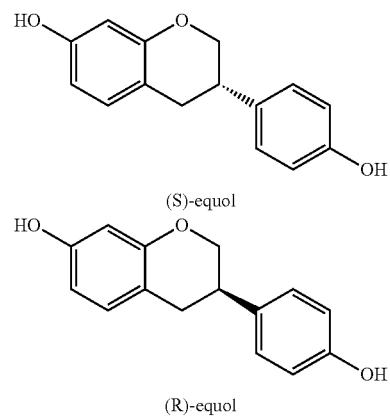

(S)-equol (R)-equol (1) Cross-reactivity to R-equol is 80% or more as compared to a cross-reactivity to S-equol as 100%. Cross-reactivity to R-equol may also be 85% or more, or may also be 90% or more. It may also be 95% or more, or may be about 98% for example. It may also be 105% or less for example.

(2) Cross-reactivity to one or two or more isoflavones selected from the group consisting of daidzein, genistein and glycitein is 0.01% or less. Furthermore, cross-reactivity to all of daidzein, genistein and glycitein may be 0.01% or less for example. Moreover, this cross-reactivity may be 0.005% or less.

(3) Cross-reactivity to one or two or more selected from the group consisting of ellagic acid dihydrate, catechin monohydrate and gallic acid is 1% or less. Furthermore, cross-reactivity to both ellagic acid dihydrate and catechin monohydrate may be 0.01% or less, or 0.005% or less for example.

(4) Cross-reactivity to apigenin and R—O-desmethylangolensin (DMA) is 0.01% or less. This cross-reactivity may also be 0.005% or less for example.

The cross-reactivity and cross-reactivity rate may be measured by methods known to those skilled in the art. For example, they may be measured by ELISA, competitive ELISA or the like.

The cross-reactivity of the antibody may be measured at any concentration range within the range of 0.1 μM to 75 μM of each isoflavone, although this is not a limitation. This concentration may also be 1 μM to 10 μM for example.

The cross-reactivity rate can be obtained as follows for example. First, a calibration curve is prepared using S-equol. Compounds including S-equol are prepared with concentrations of 1 μM and 10 μM, and reacted with the antibody at each concentration, and the S-equol concentration is calculated from the calibration curve. For example, if 10 μM of daidzein is added and detected at a concentration of 10 μM based on the calibration curve the cross-reactivity is given as 100%, while if it is detected at a concentration of 1 μM the cross-reactivity is given as 10%, and if it is detected at a concentration of 0.1 μM the cross-reactivity is given as 1%.

The antibody composition may contain two kinds of monoclonal antibodies. The amino acid sequences of the hypervariable regions of the heavy chains and light chains of these two monoclonal antibodies are specified.

The heavy chain (IgG) variable region ($V_H$ region) of the first antibody comprises hypervariable regions CDR1, CDR2 and CDR3 comprising the amino acid sequences represented by SEQ ID NOS: 1, 2 and 3, respectively. The heavy chain variable region containing the three hypervariable regions may have the amino acid sequence represented by SEQ ID NO: 10 for example. The nucleotide sequences of the polynucleotides encoding for the amino acid sequences represented by SEQ ID NOS: 1, 2, 3 and 10 are represented by SEQ ID NOS: 13, 14, 15 and 16, respectively.

The light chain variable region ($V_L$ region) of the first antibody comprises hypervariable regions CDR1', CDR2' and CDR3' comprising the amino acid sequences represented by SEQ ID NOS: 4, 5 and 6, respectively. The light chain variable region containing the three hypervariable regions may have the amino acid sequence represented by SEQ ID NO: 11 for example. It has the amino acid sequence represented by SEQ ID NO: 2. This light chain is a κ chain. The nucleotide sequences of the polynucleotides encoding for the amino acid sequences represented by SEQ ID NOS: 4, 5, 6 and 11 are represented by SEQ ID NOS: 18, 19, 20 and 21, respectively.

The heavy chain variable region ($V_H$ region) of the second antibody comprises hypervariable regions CDR1, CDR2 and CDR3 comprising the amino acid sequences represented by SEQ ID NOS: 1, 2 and 3, respectively. The heavy chain variable region containing the three hypervariable regions may have the amino acid sequence represented by SEQ ID NO: 10 for example. The nucleotide sequences of the polynucleotides encoding for the amino acid sequences represented by SEQ ID NOS: 1, 2, 3 and 10 are represented by SEQ ID NOS: 13, 14, 15 and 16, respectively.

The light chain variable region (VL region) of the second antibody comprises hypervariable regions CDR1', CDR2' and CDR3' comprising the amino acid sequences represented by SEQ ID NOS: 7, 8 and 9, respectively. The light chain variable region containing the three hypervariable regions may have the amino acid sequence represented by SEQ ID NO: 12 for example. This light chain is a κ chain. The nucleotide sequences of the polynucleotides encoding for the amino acid sequences represented by SEQ ID NOS: 7, 8, 9 and 12 are represented by SEQ ID NOS: 23, 24, 25 and 26, respectively.

The antibody composition may have an intact antibody having the ability to bind specifically to an arbitrary antigen (for example, S-equol or the like in this specification), or a part containing an antigen-binding moiety having such binding ability based on known technology at the time of this application. This antibody may assume various forms based on technical common knowledge at the time of the application and on the content disclosed below.

An "antigen-binding moiety" of an antibody means one or more fragments of an intact antibody retaining the ability to bind specifically to a particular antigen (such as S-equol). The "antigen-binding moiety" is not particularly limited, and may include various kinds of fragments or combinations of fragments such as a Fab fragment, a monovalent fragment composed of VL, VH, CL and CH1 domains; a F(ab)2 fragment, a divalent fragment composed of two Fab fragments (generally one from heavy and light chains) linked at a hinge region by a disulfide bridge; an Fd fragment composed of a VH and a CH1 domain; an Fv fragment composed of the VL and VH domains of a single arm of the antibody; a single-domain antibody (dAb) fragment composed of a VH domain; and an isolated complementarity determining region (CDR). Using recombinant methods, the antigen-binding moiety may also be linked by artificial peptide linkers that allow it to be prepared as a single protein chain in which the VL and VH regions pair to form a univalent molecule.

The antigen-binding moiety may also be incorporated into a single-domain antibody, maxi body, mini body, intrabody, diabody, triabody, tetrabody, v-NAR or bis-scFv.

The antigen-binding moiety may also be incorporated into a single-domain antibody, maxi body, mini body, intrabody, diabody, triabody, tetrabody, v-NAR or bis-scFv.

The species of origin of the antibody is not particularly limited, and differs depending on the purpose and the organism to which it is applied, but it may be a human antibody, mouse antibody, goat antibody or the like. "Human antibody" here encompasses antibodies having variable domains in which both the antibody framework and CDR region are derived from sequences of human origin. Moreover, when the antibody contains a constant region, the constant region means a region derived from such a human sequence, such as for example from a human germ line sequence or a mutant human germ line sequence. An antibody based on fragments from two or more biological species may be called a chimera antibody.

If the antibody is a monoclonal antibody, it can exhibit stable binding ability with respect to the antigen. Methods for obtaining monoclonal antibodies are well known to those skilled in the art. In addition to the methods described below, a human monoclonal antibody may be manufactured for example with a hybridoma comprising B cells obtained from a transgenic nonhuman animal (such as a transgenic mouse having a genome containing an introduced human heavy chain gene and an introduced light chain gene) fused to immortalized cells.

The antibody may also be a recombinant antibody such as a recombinant human antibody for example. Examples of recombinant human antibodies include antibodies isolated from animals (such as mice) having human immunoglobulin genes introduced by gene transfer or chromosome introduction, or from hybridomas prepared from these; antibodies isolated from host cells, such as a transfectoma, that have been transformed so as to express human antibodies; antibodies isolated from recombinant combinatorial human antibody libraries; and antibodies manufactured, expressed, prepared or isolated by other techniques including splicing of all or part of a human immunoglobulin gene sequence to another DNA sequence. Such recombinant human antibodies have variable regions in which the framework and CDR region are derived from human germ line immunoglobulin sequences.

Methods for manufacturing the antibody are described in detail below, but the antibody may also be a mutant thereof as long as it is obtained by known methods and has the ability to recognize and bind to RS-equol. For example, a new antibody can be obtained by introducing a mutation or the like to modify at least part of an antibody as a starting material, such as a complete heavy chain and/or light chain sequence, a $V_H$ and/or $V_L$ sequence, or a constant region bound thereto. A so-called peg chain can also be introduced into the resulting antibody. Such antibody modification methods are themselves well known to those skilled in the art.

The antibody may include a label as necessary. The label is not particularly limited, and a conventional known labeling substance may be selected and used appropriately. Although not particularly limited, typical examples of the labeling substance include labeling substances using fluorescence, radioactivity, enzymes (such as peroxidase or alkali phosphatase), phosphorescence, chemoluminescence, coloration or the like.

The antibody may also be provided as a label with a substance capable of binding to the label. A molecule or substance may also be provided capable of binding to these in such a way that it can ultimately be recognized by the labeling substance. These substances or the like may employ protein-protein interactions, low-molecular-weight compound-protein interactions or the like. Examples include antibodies participating in antigen-antibody reactions, biotin as part of an avidin(streptavidin)-biotin system, digoxigenin as part of an anti-digoxigenin (DIG)-digoxigenin (DIG) system, and haptens such as FITC as part of an anti-FITC-FITC system. In this case, the other molecule or substance (for example, an antigen such as streptavidin or anti-FITC) that interacts with the substance having the ability to bind with the labeling substance ultimately used for detection is modified so that it has a site for binding with the label-binding substance.

The labels of these various embodiments can be obtained commercially, and methods for labeling antibodies are well known to those skilled in the art. Therefore, a person skilled in the art can obtain various labels, and apply them to the antibody via functional groups such as amino and carboxyl groups.

(Method for Manufacturing Anti-equol Antibody)

The method for manufacturing the antibody disclosed in this specification may comprise immunizing an animal with a complex comprising a carrier protein complexed to (racemic) RS-equol, and obtaining an antibody having specific binding ability to RS-equol from a hybridoma derived from the animal's spleen cells.

The obtaining the antibody may also comprise isolating a hybridoma capable of producing an antibody with specific binding ability to RS-equol out of hybridomas obtained by fusing myeloma cells with spleen cells isolated from the animal, and using this hybridoma to produce the antibody. With this manufacturing method, the antibody of the invention, which is a monoclonal antibody, and the antibody composition of the invention can be obtained efficiently.

(Immunizationep)

The immunization is explained here. The carrier protein for obtaining the complex may be selected appropriately from known carrier proteins such as keyhole limpet hemocyanin (KLH), bovine serum albumin (BSA), ovalbumin (OVA), rabbit serum albumin (RSA) and bovine thyroglobulin (THY). The carrier protein may also be another protein derived from various vertebrates such as humans, mice, rabbits and goats, or a mutant thereof.

The complex can be obtained for example by introducing a carrier protein such as KLH by ordinary methods via the carboxyl groups of carboxymethyls introduced into the hydroxyl groups of (racemic) RS-equol. The carrier protein such as KLH can be introduced into the RS-equol by known methods. Because carboxyl groups are introduced into both the 4' and 7 position hydroxyl groups of both equols, both 4'-position complexes having the carrier protein introduced via the 4' position hydroxyl and 7-position complexes exist. Thus, out of the four possible complexes, including R-form 4'-position complex, R-form 7-position complex, S-form 4'-position complex and S-form 7-position complex, at least one R-form complex and one S-form complex can be combined and used together as the RS-equol carrier protein complex. Preferably, all these four kinds of complexes are combined. By immunizing an animal with the resulting complex, it is possible to evaluate ability to produce the antibody using specific binding with RS-equol (racemic body) as the indicator, and efficiently obtain a suitable monoclonal antibody for the antibody composition of the invention.

A vertebrate is immunized with the RS-equol-carrier protein complex thus obtained. The species of the vertebrate to be immunized (hereunder also called the immune animal) is not particularly limited, and examples include recombinant and non-recombinant non-human animals. Preferred examples include mice, rats, goats and rabbits. As discussed above, a non-human vertebrate that has been genetically modified to be able to produce human antibodies can be used to obtain a human antibody.

Administration of the immunogen to the immune animal is not particularly limited, but a known method such as intraperitoneal administration or intravenous administration may be selected as necessary. A complete adjuvant or incomplete adjuvant may also be used appropriately when administering the complex. The complex may be administered as many times as necessary for immunization. Normally, the complex is administered about 2 to 5 times.

A vertebrate can be immunized with such an antigen, an antibody titer against RS-equol can then be evaluated to confirm production of the antibody in the immune animal. Whether or not the desired antibody has been produced in the immune animal can be evaluated by collecting blood from the immune animal and evaluating antibody titer using RS-equol or the like. A known method such as ELISA can be used appropriately for the evaluation.

The spleen is removed from an immune animal that can be confirmed to have high antibody titer against RS-equol, spleen cells are prepared, cell fusion is performed by known cell fusion methods using polyethylene glycol or the like and mouse myeloma cells such as P3U1 cells, and a hybridoma is selected. Hybridomas can be selected for example by culturing for 10 to 14 days in normal medium (HAT medium), using the fact that the myeloma cell line of the hybridomas is 8-azaguanine resistant. The antibody titer of the antibodies produced by the selected hybridomas is then analyzed by ELISA using RS-equol, and a hybridoma producing an antibody with high titer is isolated by limiting dilution or the like. The isolated hybridoma is cultured in appropriate medium, and a purified monoclonal antibody can be obtained from the resulting culture supernatant by an appropriate method such as ammonium sulfate fractionation or affinity chromatography.

A monoclonal antibody (hybridoma) for application to the antibody composition can be selected by evaluating (1) cross-reactivity with R-equol as well as S-equol, and (2) to (4) cross-reactivity with the various isoflavones described above, including equol precursors.

The amino acid sequences of the resulting monoclonal antibody and its antibody fragments can be obtained by amino acid sequence analysis of the antibody and/or nucleotide sequence analysis of an antibody-coding region obtained from the hybridoma. [0047] The DNA or other polynucleotides encoding for the amino acid sequences of the heavy chain variable region and light chain variable region of the monoclonal antibody thus obtained are also one embodiment of these disclosures. A host cell carrying such an expression vector is also an embodiment of these disclosures. The expression vector may take an appropriate form known to those skilled in the art according to the host species, and control regions such as a promoter and terminator may also be selected appropriately. The polynucleotide is DNA for example, such as cDNA.

The heavy chain variable region and its ultravariable regions and the light chain variable region and its ultravariable regions of a monoclonal antibody that may be contained in the antibody composition are as explained previously.

(Method for Measuring Equol in Biological Specimen)

The equol measurement method disclosed in this specification may comprise of bringing the antibody into contact with equol in a biological specimen. In this step, the antibody binds to equol based on its specific binding ability. This equol-antibody complex can be detected by various methods or via the label attached to the antibody, to measure the presence or absence and concentration (amount) of the equol.

Methods for using antigens to detect and measure binding antigens based on the specific binding ability of the antibody are well known to those skilled in the art. Such known methods may be applied to the measurement method of the present disclosure. Examples of such known methods include not only ELISA, RIA and immunochromatography, but also complex precipitation reactions and immunoelectrophoresis, a single radial immuno-diffusion method, an immuno-electro-diffusion method and cross-immunoelectrophoresis based on the precipitation reactions; and latex agglutination using agglutination reactions of the complex, Western blotting (using oxygen immunization, chemoluminescence or the like for detection), immunohistochemical detection and the like.

The conditions for measuring the equol concentration, antibody concentration and the like in this measurement method can be set appropriately by a person skilled in the art according to the type of measurement method and the like. Because the antibody has strong antibody binding, a detection limit of 0.5 µM as equol concentration can be ensured for example in immunochromatography using a porous solid-phase carrier. The detection limit may also be an equol concentration of 0.4 µM for example, or 0.3 µM for example, or 0.2 µM for example, or 0.1 µM for example, or 0.05 µM for example. It may also be 0.04 µM for example, or 0.03 µM for example, or 0.02 µM for example, or 0.01 µM for example.

In such immunochromatography, equol concentrations at or above the detection limit, such as equol assay values in the range of 0.01 µM to 180 mM, are confirmed to correlate highly with assay values from high performance liquid chromatography (HPLC). Thus, with the antibody it is possible to detect and assay equol sensitively and accuracy even with a simple device such as an immunochromatographic device.

These measurement methods may be applied to measuring equol in various kinds of biological samples. The biological samples are not particularly limited, and various samples from animals, plants and microorganisms may be used. In the case of humans and other animals, examples include urine, blood, saliva, tears, serum, plasma, stool, tissue or tissue extracts and the like. In the case of plants, examples include foodstuffs and the like. In the case of microorganisms, examples include culture supernatant, crushed cells, cell extracts and the like.

A known method such as ELISA or antibody chromatography based on equol-antibody complex formation may be applied appropriately to S-equol detection or measurement. In this measurement method, secondary antibodies to the antibody may be used appropriately for detecting the equol-antibody complex.

(Equol Measurement Device)

The equol measurement device disclosed in this specification may include the antibody either bound to or capable of binding to a solid phase carrier. With this device, equol can be measured easily, sensitively and with high accuracy because the device uses the antibody composition having excellent detection sensitivity.

The measurement device may assume various forms. Examples of solid-phase carriers include immunochromatographic solid-phase carriers such as sticks and strips, and solid-phase carriers for arrays, such as latex beads, glass and plastic.

(Equol Measurement Kit)

The equol measurement kit disclosed in this specification may contain the antibody composition. This kit may also contain reagents for detecting the equol-antibody complex.

These reagents may include the labels mentioned above, such as a label, labeling substance and/or label-binding substance, as well as reagents for introducing these label substances and/or label-binding substances, or optionally labeled secondary antibodies, or reagents for the labeling substances (such as a substrate or the like when using a peroxidase labeling substance).

The kit may also include a blocking reagent for detection by ELISA or antibody chromatography, and cleaning solutions, buffers and the like.

Embodiments

Embodiments are given below as specific examples for explaining the disclosures of the present specification in detail. These examples are meant to explain the disclosures of the specification, and not to limit its scope.

First Embodiment (Preparation of Anti-equol Monoclonal Antibody)

(1) Preparation of Immunogen

Because equol is a low-molecular-weight molecule, it cannot serve as an antigen by itself. Therefore, 66 mg of (racemic) RS-equol (manufactured by Toronto Research Chemicals), benzyl bromoacetate, and 90 mg of potassium carbonate were left for one day at room temperature, and the ester was hydrolyzed by palladium carbon and catalytic reduction to thereby introduce carboxymethyl groups into the 4-position and 7-position carbon atoms, and obtain equol. This carboxymethyl equol was obtained as two kinds having carboxyl groups bound to the 4 and 7 positions. 20 mg of these two kinds of carboxymethyl equol, 15 mg of EDC and 21 mg of sulfo-NHS were reacted for 24 hours in DMF, and then reacted for 4 hours at 25° C. with 3 mL of a PBS solution of 46 mg of keyhole limpet hemocyanin (KLH) to thereby prepare an equol-KLH conjugate bound by an amide bond.

(2) Mouse Immunization and Establishment of Hybridoma 0.5 mg/mL PBS of the equol-KLH conjugate was mixed with an equal amount of adjuvant, and 0.15 mL was administered intraperitoneally to female BALB/c mice (6 weeks old). Two additional doses were administered every 2 weeks, and 3 days after the final immunization, the spleens were removed from the mice and fused with myeloma cells (P3U1) to prepare hybridomas. The cells were fused by mixing the spleen cells and myeloma cells at a rate of 1:5, and fusing them by ordinary methods using PEG. These were cultured for 10 to 14 days in HAT medium, after which hybridomas were selected.

The antibody titer of the supernatant was measured by the aforementioned ELISA method in the culture supernatant of wells in which hybridoma cell colonies had formed, and hybridomas producing antibodies with high antibody titer were isolated by the limiting dilution method. Screening to isolate the hybridomas was performed using RS-equol as the antigen. The isolated fused cells were cultured in 10%

DMEM medium, and purified with an IgG column to obtain monoclonal antibodies (anti-equol antibodies).

(3) Antibody Evaluation

The resulting monoclonal antibodies were subjected to amino acid sequence analysis and nucleotide sequence analysis. Two kinds of light-chain variable regions (κ and λ) and one kind of heavy chain variable region were detected. This indicates that the resulting hybridoma is a mixture of two kinds of hybridomas, and thus the resulting antibody is a mixture (composition) of two kinds of monoclonal antibodies. The amino acid sequences of the ultravariable regions and the complete amino acid sequence of the κ chain light chain variable region are represented by SEQ ID NOS: 4 to 6 and 11, while the nucleotide sequences encoding for these regions are represented by SEQ ID NOS: 18 to 21. The amino acid sequences of the ultravariable regions and the entire amino acid sequence of the λ chain light chain variable region are represented by SEQ ID NOS: 7 to 9 and 12, while the nucleotide sequences encoding for these regions are represented by SEQ ID NOS: 23 to 26. The amino acid sequences of the ultravariable regions and the total amino acid sequence of the IgG heavy chain variable region are represented by SEQ ID NOS: 1 to 3 and 10, while the nucleotide sequences encoding for these regions are represented by SEQ ID NOS: 13 to 16.

Second Embodiment (Evaluating Cross-reactivity of Anti-equol Monoclonal Antibody Composition)

To investigate the cross-reactivity of the resulting antibody composition, reactivity to 9 kinds of compounds including S-equol (S-equol, daidzein, genistein, glycitein, ellagic acid dihydrate, catechin monohydrate, gallic acid, apigenin and DMA) was investigated. First, a calibration curve was prepared using S-equol. The 9 compounds including S-equol were prepared at concentrations of 1 μM and 10 μM, and reacted with the antibody at each concentration, and cross-reactivity was calculated from the calibration curve. The results are shown in Table 1 below.

TABLE 1

| Compound name | 1 μM | 10 μM |
|---|---|---|
| R-Equol | 1.20 | 11.88 |
| S-Equol | 1.34 | 10.84 |
| Ellagic acid dihydrate | 0.00 | 0.00 |
| (+)-Catechin hydrate | 0.00 | 0.01 |
| Gallic acid | 0.00 | 0.08 |
| Daidzein | 0.00 | 0.00 |
| Genistein | 0.00 | 0.00 |
| Glycitein | 0.00 | 0.00 |
| Apigenin | 0.00 | 0.00 |
| R—O-DMA | 0.00 | 0.00 |
| Cross-reactivity with S-equol (%) | | |
| R-Equol | 89.55 | 109.59 |
| S-Equol | 100.00 | 100.00 |

TABLE 1-continued

| | 1 μM | 10 μM |
|---|---|---|
| Ellagic acid dihydrate | 0.00 | 0.00 |
| (+)-Catechin hydrate | 0.00 | 0.09 |
| Gallicacid | 0.00 | 0.74 |
| Daidzein | 0.00 | 0.00 |
| Genistein | 0.00 | 0.00 |
| Glycitein | 0.00 | 0.00 |
| Apigenin | 0.00 | 0.00 |
| R—O-DMA | 0.00 | 0.00 |

As shown in Table 1, the resulting antibody composition was specific for R-equol as well as S-equol, and exhibited only very low cross-reactivity with similar compounds.

Third Embodiment (Preparation of Equol Calibration Curve)

FIG. 1 shows a calibration curve obtained by performing immunochromatography with the resulting antibody composition using standard solutions with concentrations of 3, 1, 0.3, 0.1, 0.03, 0.01 and 0 μM obtained by serially diluting an S-equol standard solution with a maximum concentration of 3 μM with dilution buffer. As shown in FIG. 1, the calibration range was 0.01 μM to 3 μM. The antibody composition obtained in Example 1 was shown to have extremely high detection sensitivity.

Immunochromatography was performed under the following conditions using an Immunomeasure (Aisin Seiki Co., Ltd.) as the immunochromatography device. The standard solutions, a buffer and a gold colloid anti-equol antibody were each brought to room temperature, and the gold colloid antibody was dissolved in 1400 μl of the buffer to prepare an antibody solution of a specific concentration. 96 μl of the antibody solution was placed in a microtube, 4 μl each of the equol standard solutions (0, 0.01, 0.03, 0.1, 0.3, 1 and 3 μM), a urine specimen and control urine were added and mixed, and 75 μl of the mixture in the microtube was added dropwise to a specific site of the immunochromatography device and left for 20 minutes in a moisture box to develop, after which coloration by the gold colloid was detected.

Fourth Embodiment (HPLC Evaluation of Equol Measurement Results from Immunochromatography)

Figure 2:
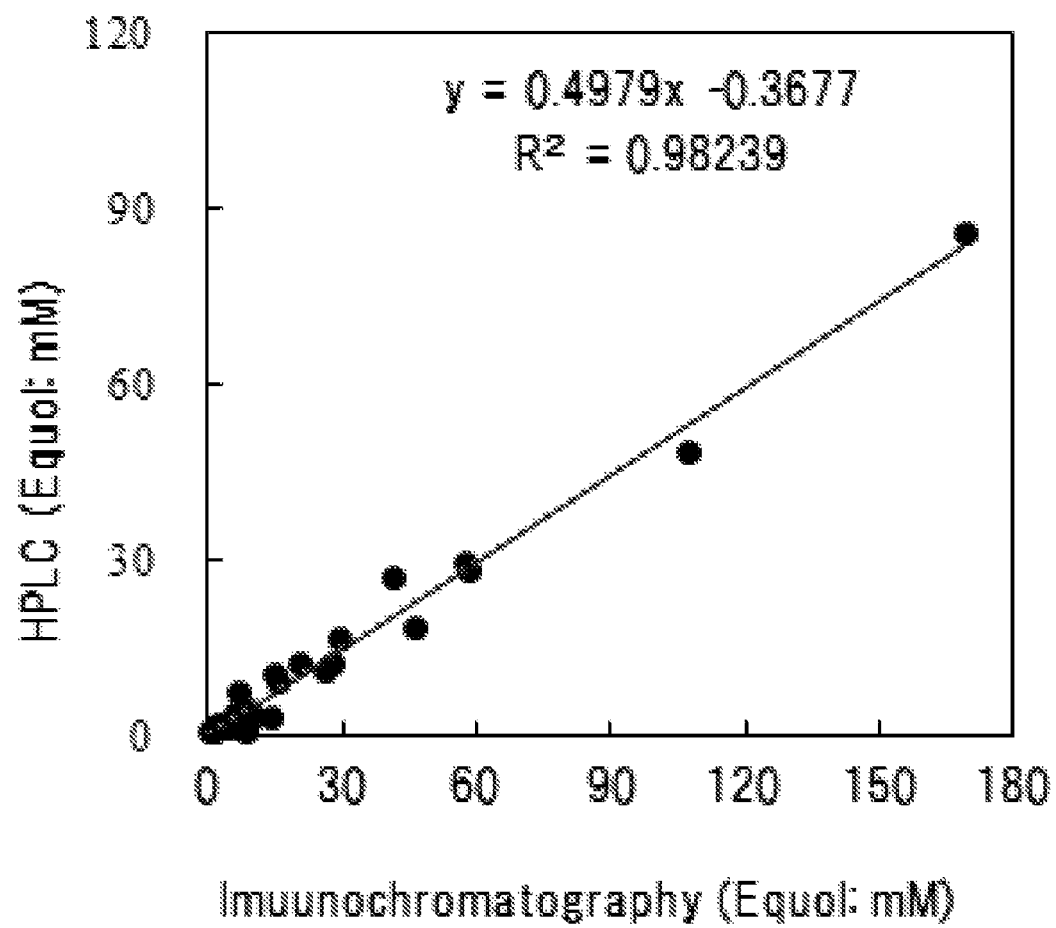
FIG. 2 shows the results of measurement of an anti-equol monoclonal antibody by HPLC and immunochromatography.

The correlation between HPLC methods used for conventional measurement and immunochromatographic measurement of the antibody composition obtained in Example 1 under the same conditions as in Embodiment 3 was evaluated for 30 specimens of human urine. The measurement results are compared in graph form in FIG. 2. As shown in FIG. 2, there is a linear relationship between the measurement method and HPLC with an approximate curve of y=0.4979x−0.3677 and a correlation coefficient of $R^2$=0.982.

Citation List

Patent Literature 1: Japanese Patent Application Publication No. 2010-169507

The invention claimed is:

1. An anti-equol antibody composition, comprising an anti-equol monoclonal antibody or an anti-equol monoclonal antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 4, a hypervariable region CDR2' comprising the amino acid sequence represented by SEQ ID NO: 5 and a hypervariable region CDR3' comprising the amino acid sequence represented by SEQ ID NO: 6; and an anti-equol monoclonal antibody or an anti-equol monoclonal antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 7, a hypervariable region CDR2' comprising the amino acid sequence represented by SEQ ID NO: 8 and a hypervariable region CDR3' comprising the amino acid sequence represented by SEQ ID NO: 9.

2. The composition according to claim 1, having 80% or more cross-reactivity, in total, to R-equol as compared to a cross-reactivity to S-equol as 100%.

3. The composition according to claim 1, wherein cross-reactivity to R-equol is 85% or more as compared to a cross-reactivity to S-equol as 100%.

4. The composition according to claim 1, also having 0.01% or less cross-reactivity to one or two or more isoflavones selected from the group consisting of daidzein, genistein and glycitein as compared to a cross-reactivity to S-equol as 100%.

5. The composition according to claim 4, wherein the cross-reactivity to each of the isoflavones including daidzein, genistein and glycitein is 0.01% or less.

6. The composition according to claim 1, also having 1% or less cross-reactivity to one or two or more selected from the group consisting of ellagic acid dihydrate, catechin monohydrate and gallic acid as compared to a cross-reactivity to S-equol as 100%.

7. The composition according to claim 6, wherein the cross-reactivity to ellagic acid dihydrate and catechin monohydrate is 0.01% or less.

8. An equol detection reagent containing the composition according to claim 1.

9. An anti-equol monoclonal antibody or an anti-equol monoclonal antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 4, a hypervariable region CDR2' comprising the amino acid sequence represented by SEQ ID NO: 5 and a hypervariable region CDR3' comprising the amino acid sequence represented by SEQ ID NO: 6.

10. An anti-equol monoclonal antibody or an anti-equol monoclonal antibody fragment thereof comprising, as an immunoglobulin heavy chain variable region, a heavy chain hypervariable region CDR1 comprising the amino acid sequence represented by SEQ ID NO: 1, a hypervariable region CDR2 comprising the amino acid sequence represented by SEQ ID NO: 2 and a hypervariable region CDR3 comprising the amino acid sequence represented by SEQ ID NO: 3, and as an immunoglobulin light chain variable region, a hypervariable region CDR1' comprising the amino acid sequence represented by SEQ ID NO: 7, a hypervariable region CDR2' comprising the amino acid sequence represented by SEQ ID NO: 8 and a hypervariable region CDR3' comprising the amino acid sequence represented by SEQ ID NO: 9.

11. A method for measuring equol in a biological sample, comprising bringing the equol detection reagent according to claim 8 into contact with the equol in the biological sample.

12. An equol measurement device including the detection reagent according to claim 8, wherein the detection reagent is bound to a solid-phase carrier.

13. An equol measurement kit including the detection reagent according to claim 8.

14. An expression vector containing a polynucleotide encoding for the antibody or antibody fragment thereof according to claim 9.

15. An expression vector containing a polynucleotide encoding for the antibody or antibody fragment thereof according to claim 10.

* * * * *

SEQUENCE LISTING

<160> NUMBER OF SEQ ID NOS: 27

<210> SEQ ID NO 1
<211> LENGTH: 5
<212> TYPE: PRT
<213> ORGANISM: Mus musculus

```
<400> SEQUENCE: 1

Ala Tyr Ala Trp Asn
1               5

<210> SEQ ID NO 2
<211> LENGTH: 16
<212> TYPE: PRT
<213> ORGANISM: Mus musculus

<400> SEQUENCE: 2

Met Gly Tyr Ile Ser Tyr Ser Gly Ser Ser Tyr Tyr Asn Pro Ser Leu
1               5                   10                  15

<210> SEQ ID NO 3
<211> LENGTH: 11
<212> TYPE: PRT
<213> ORGANISM: Mus musculus

<400> SEQUENCE: 3

Ala Gln Gly Ile Phe Gly Asn Leu Gly Asp Tyr
1               5                   10

<210> SEQ ID NO 4
<211> LENGTH: 12
<212> TYPE: PRT
<213> ORGANISM: Mus musculus

<400> SEQUENCE: 4

Lys Ser Val Ser Thr Ser Gly Tyr Ser Tyr Met His
1               5                   10

<210> SEQ ID NO 5
<211> LENGTH: 7
<212> TYPE: PRT
<213> ORGANISM: Mus musculus

<400> SEQUENCE: 5

Leu Val Ser Asn Leu Glu Ser
1               5

<210> SEQ ID NO 6
<211> LENGTH: 9
<212> TYPE: PRT
<213> ORGANISM: Mus musculus

<400> SEQUENCE: 6

Gln His Ile Arg Glu Leu Thr Arg Ser
1               5

<210> SEQ ID NO 7
<211> LENGTH: 14
<212> TYPE: PRT
<213> ORGANISM: Mus musculus

<400> SEQUENCE: 7

Arg Leu Ser Thr Gly Ala Val Thr Ser Arg Asn Tyr Ala Asn
1               5                   10

<210> SEQ ID NO 8
<211> LENGTH: 7
<212> TYPE: PRT
<213> ORGANISM: Mus musculus

<400> SEQUENCE: 8
```

Gly Thr Asn Asn Arg Ala Pro
1               5

<210> SEQ ID NO 9
<211> LENGTH: 9
<212> TYPE: PRT
<213> ORGANISM: Mus musculus

<400> SEQUENCE: 9

Ala Leu Trp Tyr Ser Asn His Trp Val
1               5

<210> SEQ ID NO 10
<211> LENGTH: 155
<212> TYPE: PRT
<213> ORGANISM: Mus musculus

<400> SEQUENCE: 10

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Ala Tyr Ala Trp Asn Trp Ile Arg Gln Phe Pro Gly Asn Lys Leu
        50                  55                  60

Glu Trp Met Gly Tyr Ile Ser Tyr Ser Gly Ser Ser Tyr Tyr Asn Pro
65                  70                  75                  80

Ser Leu Lys Ser Arg Ile Ser Ile Thr Arg Asp Thr Ser Lys Asn Gln
                85                  90                  95

Phe Phe Leu His Leu Asn Ser Val Thr Thr Glu Asp Thr Ala Thr Tyr
            100                 105                 110

Tyr Cys Ala Gln Gly Ile Phe Gly Asn Leu Gly Asp Tyr Trp Gly Gln
        115                 120                 125

Gly Thr Thr Leu Thr Val Ser Ser Ala Lys Thr Thr Pro Pro Ser Val
        130                 135                 140

Tyr Pro Leu Ala Pro Gly Ser Ala Ala Gln Thr
145                 150                 155

<210> SEQ ID NO 11
<211> LENGTH: 128
<212> TYPE: PRT
<213> ORGANISM: Mus musculus

<400> SEQUENCE: 11

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Tyr Arg Ala Ser Lys Ser
            35                  40                  45

Val Ser Thr Ser Gly Tyr Ser Tyr Met His Trp Asn Gln Gln Lys Pro
        50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys 100                 105                 110
Gln His Ile Arg Glu Leu Thr Arg Ser Glu Gly Gly Pro Ser Trp Lys
        115                 120                 125

<210> SEQ ID NO 12
<211> LENGTH: 156
<212> TYPE: PRT
<213> ORGANISM: Mus musculus

<400> SEQUENCE: 12

Met Ala Trp Thr Ser Leu Ile Leu Ser Leu Leu Ala Leu Ser Ser Gly
1               5                   10                  15

Val Ile Ser Gln Ala Val Val Thr Gln Glu Ser Val Ile Thr Thr Ser
            20                  25                  30

Pro Gly Glu Thr Val Thr Leu Thr Cys Arg Leu Ser Thr Gly Ala Val
        35                  40                  45

Thr Ser Arg Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Val Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

Gly Gln Pro Lys Ser Ser Pro Ser Val Thr Leu Phe Pro Pro Ser Thr
    130                 135                 140

Glu Glu Leu Ser Leu Gly Ile Gly Ser Pro Gly Thr
145                 150                 155

<210> SEQ ID NO 13
<211> LENGTH: 15
<212> TYPE: DNA
<213> ORGANISM: Mus musculus

<400> SEQUENCE: 13
gcttatgcct ggaac                                                    15

<210> SEQ ID NO 14
<211> LENGTH: 48
<212> TYPE: DNA
<213> ORGANISM: Mus musculus

<400> SEQUENCE: 14
atgggctaca taagctacag tggtagctct tactacaacc catctctc                48

<210> SEQ ID NO 15
<211> LENGTH: 33
<212> TYPE: DNA
<213> ORGANISM: Mus musculus

<400> SEQUENCE: 15
gcgcagggaa tctttggtaa cctaggtgac tac                                33

<210> SEQ ID NO 16
<211> LENGTH: 465
<212> TYPE: DNA
<213> ORGANISM: Mus musculus
<220> FEATURE:

```
<221> NAME/KEY: CDS
<222> LOCATION: (1)..(465)

<400> SEQUENCE: 16
```

| | | | | | | | | | | | | | | | | |
|---|---|---|---|---|---|---|---|---|---|---|---|---|---|---|---|---|
| atg | aga | gtg | ctg | att | ctt | ttg | tgg | ctg | ttc | aca | gcc | ttt | cct | ggt | atc | 48 |
| Met | Arg | Val | Leu | Ile | Leu | Leu | Trp | Leu | Phe | Thr | Ala | Phe | Pro | Gly | Ile | |
| 1 | | | | 5 | | | | | 10 | | | | | 15 | | |
| ctg | tct | gat | gtg | cag | ctt | cag | gag | tcg | gga | cct | ggc | ctg | gtg | aaa | cct | 96 |
| Leu | Ser | Asp | Val | Gln | Leu | Gln | Glu | Ser | Gly | Pro | Gly | Leu | Val | Lys | Pro | |
| | | | 20 | | | | | 25 | | | | | 30 | | | |
| tct | cag | tct | ctg | tcc | ctc | acc | tgc | act | gtc | act | ggc | tac | tca | atc | acc | 144 |
| Ser | Gln | Ser | Leu | Ser | Leu | Thr | Cys | Thr | Val | Thr | Gly | Tyr | Ser | Ile | Thr | |
| | | 35 | | | | | 40 | | | | | 45 | | | | |
| agt | gct | tat | gcc | tgg | aac | tgg | atc | cgg | cag | ttt | cca | gga | aac | aaa | ctg | 192 |
| Ser | Ala | Tyr | Ala | Trp | Asn | Trp | Ile | Arg | Gln | Phe | Pro | Gly | Asn | Lys | Leu | |
| | 50 | | | | | 55 | | | | | 60 | | | | | |
| gag | tgg | atg | ggc | tac | ata | agc | tac | agt | ggt | agc | tct | tac | tac | aac | cca | 240 |
| Glu | Trp | Met | Gly | Tyr | Ile | Ser | Tyr | Ser | Gly | Ser | Ser | Tyr | Tyr | Asn | Pro | |
| 65 | | | | | 70 | | | | | 75 | | | | | 80 | |
| tct | ctc | aaa | agt | cga | atc | tct | atc | act | cga | gac | aca | tcc | aag | aac | cag | 288 |
| Ser | Leu | Lys | Ser | Arg | Ile | Ser | Ile | Thr | Arg | Asp | Thr | Ser | Lys | Asn | Gln | |
| | | | | 85 | | | | | 90 | | | | | 95 | | |
| ttc | ttc | ctg | cac | ttg | aat | tct | gtg | act | act | gag | gac | aca | gcc | aca | tat | 336 |
| Phe | Phe | Leu | His | Leu | Asn | Ser | Val | Thr | Thr | Glu | Asp | Thr | Ala | Thr | Tyr | |
| | | | 100 | | | | | 105 | | | | | 110 | | | |
| tac | tgt | gcg | cag | gga | atc | ttt | ggt | aac | cta | ggt | gac | tac | tgg | ggc | caa | 384 |
| Tyr | Cys | Ala | Gln | Gly | Ile | Phe | Gly | Asn | Leu | Gly | Asp | Tyr | Trp | Gly | Gln | |
| | | 115 | | | | | 120 | | | | | 125 | | | | |
| ggc | acc | act | ctc | aca | gtc | tcc | tca | gcc | aaa | acg | aca | ccc | cca | tct | gtc | 432 |
| Gly | Thr | Thr | Leu | Thr | Val | Ser | Ser | Ala | Lys | Thr | Thr | Pro | Pro | Ser | Val | |
| | 130 | | | | | 135 | | | | | 140 | | | | | |
| tat | cca | ctg | gcc | cct | gga | tct | gct | gcc | caa | act | | | | | | 465 |
| Tyr | Pro | Leu | Ala | Pro | Gly | Ser | Ala | Ala | Gln | Thr | | | | | | |
| 145 | | | | 150 | | | | | 155 | | | | | | | |

```
<210> SEQ ID NO 17
<211> LENGTH: 155
<212> TYPE: PRT
<213> ORGANISM: Mus musculus

<400> SEQUENCE: 17
```

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Ala Tyr Ala Trp Asn Trp Ile Arg Gln Phe Pro Gly Asn Lys Leu
    50                  55                  60

Glu Trp Met Gly Tyr Ile Ser Tyr Ser Gly Ser Ser Tyr Tyr Asn Pro
65                  70                  75                  80

Ser Leu Lys Ser Arg Ile Ser Ile Thr Arg Asp Thr Ser Lys Asn Gln
                85                  90                  95

Phe Phe Leu His Leu Asn Ser Val Thr Thr Glu Asp Thr Ala Thr Tyr
            100                 105                 110

Tyr Cys Ala Gln Gly Ile Phe Gly Asn Leu Gly Asp Tyr Trp Gly Gln
        115                 120                 125

Gly Thr Thr Leu Thr Val Ser Ser Ala Lys Thr Thr Pro Pro Ser Val
    130                 135                 140

```
Tyr Pro Leu Ala Pro Gly Ser Ala Ala Gln Thr
145                 150                 155

<210> SEQ ID NO 18
<211> LENGTH: 36
<212> TYPE: DNA
<213> ORGANISM: Mus musculus

<400> SEQUENCE: 18
aaaagtgtca gtacatctgg ctatagttat atgcac                              36

<210> SEQ ID NO 19
<211> LENGTH: 21
<212> TYPE: DNA
<213> ORGANISM: Mus musculus

<400> SEQUENCE: 19
cttgtatcca acctagaatc t                                              21

<210> SEQ ID NO 20
<211> LENGTH: 27
<212> TYPE: DNA
<213> ORGANISM: Mus musculus

<400> SEQUENCE: 20
cagcacatta gggagcttac acgttcg                                        27

<210> SEQ ID NO 21
<211> LENGTH: 387
<212> TYPE: DNA
<213> ORGANISM: Mus musculus
<220> FEATURE:
<221> NAME/KEY: CDS
<222> LOCATION: (1)..(387)

<400> SEQUENCE: 21 atg gag aca gac aca ctc ctg tta tgg gta ctg ctc tgg gtt cca         48
Met Glu Thr Asp Thr Leu Leu Leu Trp Val Leu Leu Trp Val Pro
1               5                   10                  15 ggt tcc act ggt gac att gtg ctg aca cag tct cct gct tcc tta gct    96
Gly Ser Thr Gly Asp Ile Val Leu Thr Gln Ser Pro Ala Ser Leu Ala
            20                  25                  30 gta tct ctg ggg cag agg gcc acc atc tca tac agg gcc agc aaa agt    144
Val Ser Leu Gly Gln Arg Ala Thr Ile Ser Tyr Arg Ala Ser Lys Ser
        35                  40                  45 gtc agt aca tct ggc tat agt tat atg cac tgg aac caa cag aaa cca    192
Val Ser Thr Ser Gly Tyr Ser Tyr Met His Trp Asn Gln Gln Lys Pro
    50                  55                  60 gga cag cca ccc aga ctc ctc atc tat ctt gta tcc aac cta gaa tct    240
Gly Gln Pro Pro Arg Leu Leu Ile Tyr Leu Val Ser Asn Leu Glu Ser
65                  70                  75                  80 ggg gtc cct gcc agg ttc agt ggc agt ggg tct ggg aca gac ttc acc    288
Gly Val Pro Ala Arg Phe Ser Gly Ser Gly Ser Gly Thr Asp Phe Thr
                85                  90                  95 ctc aac atc cat cct gtg gag gag gag gat gct gca acc tat tac tgt    336
Leu Asn Ile His Pro Val Glu Glu Glu Asp Ala Ala Thr Tyr Tyr Cys
            100                 105                 110 cag cac att agg gag ctt aca cgt tcg gag ggg gga cca agc tgg aaa    384
Gln His Ile Arg Glu Leu Thr Arg Ser Glu Gly Gly Pro Ser Trp Lys
        115                 120                 125 taa                                                                 387
```

<210> SEQ ID NO 22
<211> LENGTH: 128
<212> TYPE: PRT
<213> ORGANISM: Mus musculus

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ile Arg Glu Leu Thr Arg Ser Glu Gly Gly Pro Ser Trp Lys
        115                 120                 125

<210> SEQ ID NO 23
<211> LENGTH: 42
<212> TYPE: DNA
<213> ORGANISM: Mus musculus

<400> SEQUENCE: 23
cgcttaagta ctggggctgt tacaagtagg aactatgcca ac                                42

<210> SEQ ID NO 24
<211> LENGTH: 21
<212> TYPE: DNA
<213> ORGANISM: Mus musculus

<400> SEQUENCE: 24
ggtaccaaca accgagctcc a                                                       21

<210> SEQ ID NO 25
<211> LENGTH: 27
<212> TYPE: DNA
<213> ORGANISM: Mus musculus

<400> SEQUENCE: 25
gctctatggt acagcaacca ttgggtg                                                 27

<210> SEQ ID NO 26
<211> LENGTH: 468
<212> TYPE: DNA
<213> ORGANISM: Mus musculus
<220> FEATURE:
<221> NAME/KEY: CDS
<222> LOCATION: (1)..(468)

<400> SEQUENCE: 26 atg gcc tgg act tct ctt ata ctc tct ctc ctg gct ctc agc tca ggg              48
Met Ala Trp Thr Ser Leu Ile Leu Ser Leu Leu Ala Leu Ser Ser Gly
1               5                   10                  15 gtc atc tcc cag gct gtt gtg act cag gaa tct gta atc acc aca tca              96
Val Ile Ser Gln Ala Val Val Thr Gln Glu Ser Val Ile Thr Thr Ser

```
                  20                  25                  30
cct ggt gaa aca gtc aca ctc act tgt cgc tta agt act ggg gct gtt      144
Pro Gly Glu Thr Val Thr Leu Thr Cys Arg Leu Ser Thr Gly Ala Val
             35                  40                  45 aca agt agg aac tat gcc aac tgg gtc caa gaa aaa cca gat cat tta      192
Thr Ser Arg Asn Tyr Ala Asn Trp Val Gln Glu Lys Pro Asp His Leu
 50                  55                  60 ttc act ggt cta ata ggt ggt acc aac aac cga gct cca ggt gtt cct      240
Phe Thr Gly Leu Ile Gly Gly Thr Asn Asn Arg Ala Pro Gly Val Pro
 65                  70                  75                  80 gcc aga ttc tca ggc tcc ctg att gga gac aag gct gtc ctc acc atc      288
Ala Arg Phe Ser Gly Ser Leu Ile Gly Asp Lys Ala Val Leu Thr Ile
                 85                  90                  95 aca ggg gca cag act gag gat gag gca ata tat ttc tgt gct cta tgg      336
Thr Gly Ala Gln Thr Glu Asp Glu Ala Ile Tyr Phe Cys Ala Leu Trp
            100                 105                 110 tac agc aac cat tgg gtg ttc ggt gga gga acc aaa ctg act gtc cta      384
Tyr Ser Asn His Trp Val Phe Gly Gly Gly Thr Lys Leu Thr Val Leu
            115                 120                 125 ggc cag ccc aag tct tcg cca tca gtc acc ctg ttt cca ccc tcc aca      432
Gly Gln Pro Lys Ser Ser Pro Ser Val Thr Leu Phe Pro Pro Ser Thr
            130                 135                 140 gaa gag cta agc ttg gga atc gga tcc ccg ggt acc                      468
Glu Glu Leu Ser Leu Gly Ile Gly Ser Pro Gly Thr
145                 150                 155

<210> SEQ ID NO 27
<211> LENGTH: 156
<212> TYPE: PRT
<213> ORGANISM: Mus musculus

<400> SEQUENCE: 27

Met Ala Trp Thr Ser Leu Ile Leu Ser Leu Leu Ala Leu Ser Ser Gly
 1               5                  10                  15

Val Ile Ser Gln Ala Val Val Thr Gln Glu Ser Val Ile Thr Thr Ser
             20                  25                  30

Pro Gly Glu Thr Val Thr Leu Thr Cys Arg Leu Ser Thr Gly Ala Val
             35                  40                  45

Thr Ser Arg Asn Tyr Ala Asn Trp Val Gln Glu Lys Pro Asp His Leu
 50                  55                  60

Phe Thr Gly Leu Ile Gly Gly Thr Asn Asn Arg Ala Pro Gly Val Pro
 65                  70                  75                  80

Ala Arg Phe Ser Gly Ser Leu Ile Gly Asp Lys Ala Val Leu Thr Ile
                 85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
            115                 120                 125

Gly Gln Pro Lys Ser Ser Pro Ser Val Thr Leu Phe Pro Pro Ser Thr
            130                 135                 140

Glu Glu Leu Ser Leu Gly Ile Gly Ser Pro Gly Thr
145                 150                 155
```